(12) United States Patent
Osborne

(10) Patent No.: US 8,034,036 B2
(45) Date of Patent: Oct. 11, 2011

(54) PORTABLE EYE FLUSHING SYSTEM AND METHOD

(76) Inventor: Tom Osborne, Corbin, KY (US)

( * ) Notice: Subject to any disclaimer, the term of this patent is extended or adjusted under 35 U.S.C. 154(b) by 665 days.

(21) Appl. No.: 12/075,351

(22) Filed: Mar. 11, 2008

(65) Prior Publication Data

US 2008/0255527 A1 Oct. 16, 2008

Related U.S. Application Data

(60) Provisional application No. 60/922,636, filed on Apr. 10, 2007.

(51) Int. Cl.
*A61H 35/02* (2006.01)
*A61M 35/00* (2006.01)
*A61M 11/00* (2006.01)

(52) U.S. Cl. .................. 604/301; 128/200.14

(58) Field of Classification Search ............... 604/94.01, 604/289–290, 301–302, 521, 294–300; 239/358, 239/426; 128/200.14; 4/620
See application file for complete search history.

(56) References Cited

U.S. PATENT DOCUMENTS

| | | | | | |
|---|---|---|---|---|---|
| 676,379 | A | * | 6/1901 | Young | 601/37 |
| 852,827 | A | * | 5/1907 | Dorment | 601/13 |
| 1,246,971 | A | * | 11/1917 | Maier | 604/297 |
| 1,603,727 | A | * | 10/1926 | Vilas | 604/298 |
| 1,692,143 | A | * | 11/1928 | Strunz | 604/301 |
| 1,767,080 | A | * | 6/1930 | King | 604/301 |
| 1,966,557 | A | * | 7/1934 | Michelson | 604/297 |
| 2,080,268 | A | * | 5/1937 | Harris | 604/298 |
| 2,219,604 | A | * | 10/1940 | Trotter | 222/207 |
| 2,328,627 | A | * | 9/1943 | Eddins | 604/301 |
| 2,524,720 | A | * | 10/1950 | Watrous | 604/296 |
| 2,754,821 | A | * | 7/1956 | Burbig et al. | 604/298 |
| 2,826,194 | A | * | 3/1958 | Golden | 128/200.14 |
| 3,200,817 | A | * | 8/1965 | Brainard | 128/200.14 |
| 3,314,426 | A | * | 4/1967 | Carroll | 128/200.14 |
| 3,640,274 | A | * | 2/1972 | Costello | 128/200.14 |
| 3,871,554 | A | * | 3/1975 | Huck | 222/96 |
| 3,917,119 | A | * | 11/1975 | Kahn | 222/108 |
| 3,945,381 | A | * | 3/1976 | Silver | 604/301 |
| 4,002,168 | A | * | 1/1977 | Petterson | 604/298 |
| 4,012,798 | A | * | 3/1977 | Liautaud | 4/620 |
| 4,111,200 | A | * | 9/1978 | Sbarra et al. | 604/298 |
| 4,131,115 | A | * | 12/1978 | Peng | 604/297 |
| 4,493,119 | A | * | 1/1985 | Baumann | 4/620 |
| 4,641,384 | A | * | 2/1987 | Landsberger et al. | 4/620 |
| 5,037,406 | A | * | 8/1991 | Smith et al. | 604/301 |
| 5,157,798 | A | * | 10/1992 | Van Kammen | 4/620 |
| 5,373,973 | A | * | 12/1994 | Foster | 222/324 |
| 5,566,406 | A | * | 10/1996 | Demeny et al. | 4/620 |
| 5,588,564 | A | * | 12/1996 | Hutson et al. | 222/383.1 |
| 6,261,275 | B1 | * | 7/2001 | Hayes | 604/294 |
| 6,540,726 | B1 | * | 4/2003 | Follman et al. | 604/294 |
| 6,736,802 | B1 | * | 5/2004 | Recanati | 604/295 |
| 7,621,897 | B1 | * | 11/2009 | Berke | 604/295 |
| 2003/0029931 | A1 | * | 2/2003 | Zanma et al. | 239/251 |
| 2004/0111070 | A1 | * | 6/2004 | Hanley | 604/295 |

(Continued)

*Primary Examiner* — Melanie Hand
*Assistant Examiner* — Paula Craig
(74) *Attorney, Agent, or Firm* — Stockwell & Smedley, PSC

(57) ABSTRACT

Embodiments of the present invention relate to an adapter that fits over a convenient water source. The adapter includes a tube that provides a passageway for the fluid to reach the top of the adapter. At the top, there is an eye-cup with an internal delivery means for directing the fluid to a user's eye. In this manner, a user can flush their eye in a convenient, portable, and clean manner.

19 Claims, 4 Drawing Sheets

U.S. PATENT DOCUMENTS

| | | | |
|---|---|---|---|
| 2004/0164099 A1* | 8/2004 | Diestelhorst et al. | 222/190 |
| 2005/0165368 A1* | 7/2005 | Py et al. | 604/289 |
| 2005/0217019 A1* | 10/2005 | Johnson et al. | 4/620 |
| 2006/0258993 A1* | 11/2006 | Hochrainer et al. | 604/289 |
| 2007/0089234 A1* | 4/2007 | Copeland et al. | 4/620 |
| 2007/0204398 A1* | 9/2007 | Dubois | 4/620 |
| 2008/0039807 A1* | 2/2008 | Pine | 604/300 |
| 2009/0207373 A1* | 8/2009 | Stinson | 351/158 |

* cited by examiner

PORTABLE EYE FLUSHING SYSTEM AND METHOD

RELATED APPLICATIONS

The present application claims priority to provisional Patent Application Ser. No. 60/922,636 filed Apr. 10, 2007, the disclosure of which is incorporated by reference herein, in its entirety.

BACKGROUND OF THE INVENTION

1. Field of the Invention

The present invention relates generally to flushing a person's eye with fluid and more particularly with an adapter and method for its use that attaches to a readily available fluid source.

2. Description of Related Art

There are a variety of equipment and techniques available to assist a person in flushing or washing their eyes to remove particles or other types of debris. Many such systems are utilized in industrial applications where it is convenient to have a free-standing apparatus that is permanently connected to a fluid source. There are even portable devices for such applications that are about the size of a normal sink that is mounted to a movable platform and having a self-contained fluid supply.

At the other end of the spectrum are specialized eye flush kits for use by paramedics or others in the medical profession. These kits sometimes include a special bottle and attached eye-cup that is arranged as an integral unit. There are also eye-cups that are sold separately that a user can fill and then tilt their head back and invert the eye-cup over the eye. In each instance, water or other fluid is likely to travel to places other than the eye, such as the user's face or clothes. Secondly, there is little convenience in carrying around a supply of fluid that can only be used to flush a person's eye if it becomes necessary.

Thus, there remains the need for a portable eye flushing system that is convenient to use, minimizes the inherent mess of such an application, and can utilize nearby fluid sources that happen to be available.

BRIEF SUMMARY OF THE INVENTION

Embodiments of the present invention relate to an adapter that fits over a convenient water source. The adapter includes a tube that provides a passageway for the fluid to reach the top of the adapter. At the top, there is an eye-cup with an internal delivery means for directing the fluid to a user's eye. In this manner, a user can flush their eye in a convenient, portable, and clean manner.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF DRAWINGS

Various aspects of an eye flushing system are illustrated by way of example, and not by way of limitation, in the accompanying drawings, wherein.

DETAILED DESCRIPTION OF INVENTION

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Figure 1:
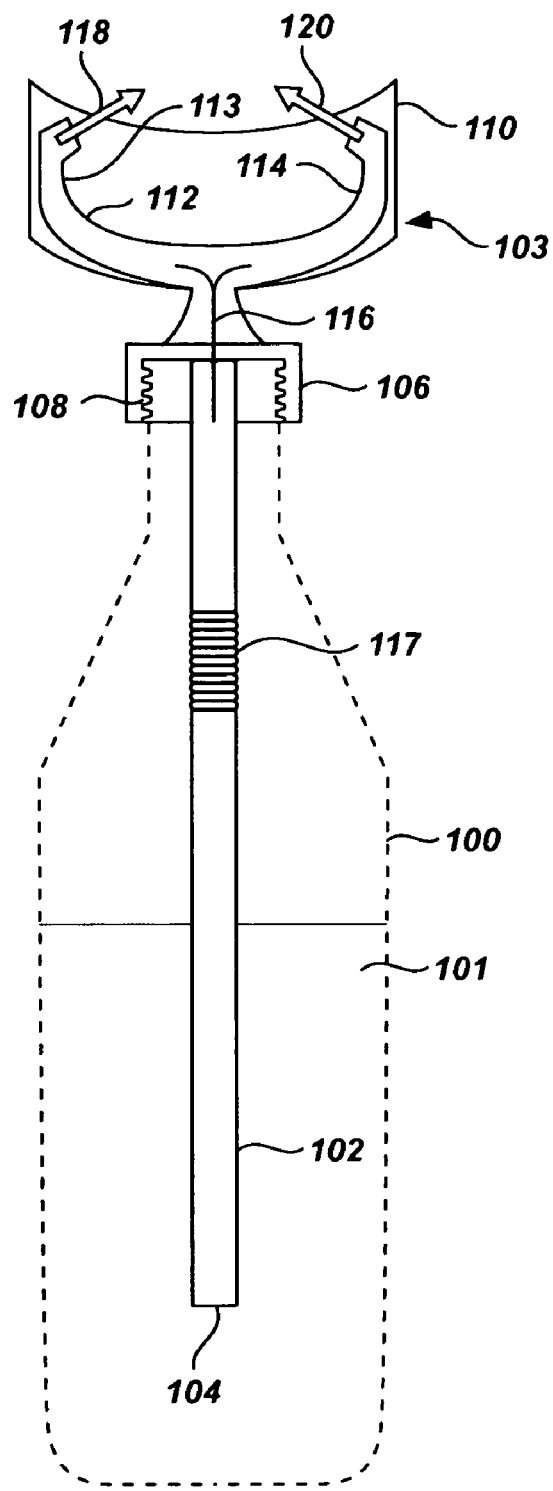
FIG. 1 shows an exemplary embodiment of an eye flushing system in accordance with the principles of the present invention.

FIG. 1 illustrates one embodiment of the present invention. In particular, a fluid bottle 100, such as a water bottle, internally holds a fluid 101 but also supports eye flushing adapter 103. The adapter 103 includes an eye cup portion 110, a neck portion 106 that attaches to the top of the water bottle 100, and a tube 102 that descends into the fluid 101. In operation, squeezing of the bottle 100 will force some of fluid 101 into the tube 102 and upwardly towards the eye cup portion 110.

As mentioned briefly, the adapter 103 attaches to the water bottle 100 via the neck portion 106. More particularly, there are internal threads in the neck portion 106 that complement the external threads 108 on the top of the water bottle 100. Thus, the adapter 103 may be simply placed over the water bottle 100 and screwed on like the original cap that came with the water bottle 100. Thus, the internal thread size must match the external threads 108 of the bottle 100 for the adapter to properly fit the bottle 100 and make a leak-proof seal.

However, many water bottles commercially available have a standard 8 threads-per-inch size that can be easily accommodated by the present adapter 103. This standard size is present in bottles as small as 8 ounces to ones holding a liter or more. Thus, the present adapter can be used with a variety of water bottles that will likely be available to a user in most circumstances.

The tubing 102 that extends into the bottle 100 can be constructed of any of a variety of different materials, having a variety of different lengths, without departing from the scope of the present invention. In general, a 7-inch tube 102 may be utilized in most bottle applications. Additionally, even though the tubing 102 is depicted in FIG. 1 as a rigid structure, the tube 102 may be relatively flexible such that it will curl or coil around the bottom of the bottle 100 if the bottle 100 is small enough. If such a flexible tube is used, then the housing 110 of the adapter 103 may have a shape that assists in coiling the tube around the housing 110 to help make the entire system compact during storage. As an additional measure, the tube 102 may have a portion 117 that is accordion-like such that it can be expanded or contracted to changes the length of the tube 102.

The tube 102 includes an opening 104 at its far end and is hollow along its length. Thus, the tube 102 provides a fluid passageway for the fluid 101 to reach the neck portion 106. The neck portion is also hollow on its inside so that it provides the fluid (depicted as arrows 116) to the eye cup portion 110. One exemplary size for the inner diameter of the tube 102 is ¼ inches. This size tube will provide an appropriate volume of water at a safe pressure when utilizing the eye cup configuration of FIG. 1. Depending on the exact shape and size of the fluid passageways at the top of the eye cup, a different size tube 102 may be utilized as well.

The adapter 103 has an eye cup portion 110 having an outer housing forms the "cup" part. Within the cup part are two arms 112, 114 extending away from one another and then upwardly. At the end of each arm, they are angled 113 back towards the center of the cup part. The particular height of the arms 112, 114 and the specific angle 113 at the ends of the arms 112, 114 can vary according to design. However, one exemplary design places the top of each arm 112, 114 about ⅛ inch below the top of the housing. At this height, the angle 113 of the top of the arms 112, 114 is about 20°. As mentioned, different heights and angles may be used without departing from the scope of the present invention.

Each arm 112, 114 is hollow, having an inner diameter of about 0.25 inches and an opening near the top for fluid to exit (shown by arrows 118, 120). Thus, each arm 112, 114 provides a fluid passage from the neck portion 106 to the point at which water is directed to a person's eye.

Figure 2A:
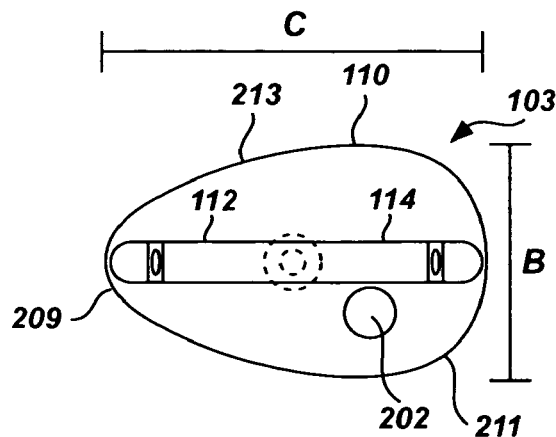
FIG. 2A shows detailed view of an eye-cup in accordance with the principles of the present invention.

FIG. 2A shows a detailed top view of the eye cup portion 110 which depicts its generally elliptical shape or egg shape. As for one example of possible dimensions of the cup of 110, the diameter of the drain hole 202 may be ⅜ inches; the length C may be about 2½ inches; the width B may be about 1½ inches; the radius of the curved portion 209 may be about 0.375 inches, the radius of the curved portion 213 may be about 6 inches; and the radius of the curved portion 211 may be about ¾ inches. These exemplary sizes are provided by way of example only and are not intended to limit the present invention to only this size eye cup. Although the exemplary sizes of FIG. 2A are typical for a majority of people, it is contemplated that both smaller and larger eye cups may be used to accommodate people of different sizes.

In FIG. 2A, the drain hole 202 is visible. This drain hole lets fluid exit the eye cup 110 in a controlled and directed manner. Without the drain hole 202, fluid may unintentionally exit the eye cup 103 at any part of its periphery during use.

Figure 2B:
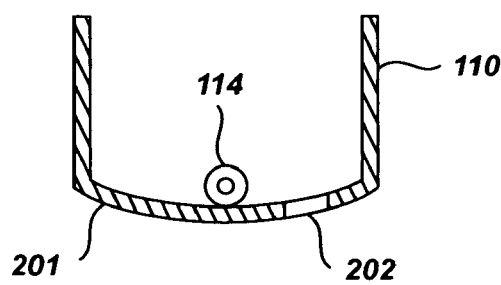
FIGS. 2B and 2C show different cut-away views of the eye-cup of FIG. 2A.
Figure 2C:
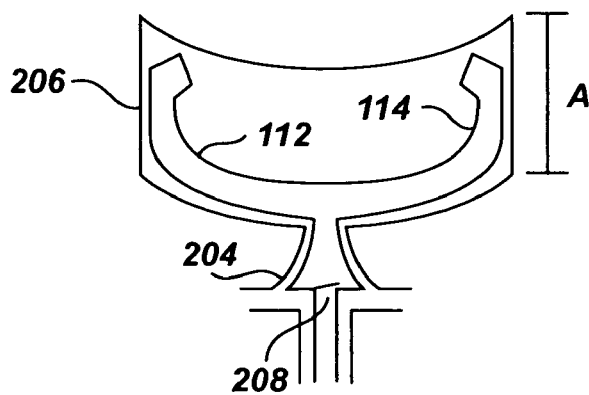

FIG. 2B shows cut-away view of the cup 110 that illustrates the relative location of one of the arms 114, the drain hole 202 and the eye cup housing. This figure illustrates that the bottom portion 201 of the eye cup portion 110 may be curved, such as, for example, having a radius of curvature of about 2¼ inches. FIG. 2C shows a different cut-away view of the adapter 103. From this view, the height A of the sides 206 of the eye cup portion housing 110 is shown relative to that of the arms 112, 114. An exemplary height A is about 1 inch and also, an exemplary radius of curvature 204 is about ⅓ inches for a transition portion between the neck part 106 and the eye cup 110. As shown in FIG. 2C, a one-way valve 208, such as, for example, a flapper valve, may be installed in this transition portion if desired because doing so would prevent any fluid from returning back into the bottle 100.

In FIG. 2B and the previous figures, the arms 112, 114 are shown as solid tubes having openings at their respective ends to expel fluid. Alternatively, the arms 112, 114 could be perforated for all or just a portion of their lengths. In this manner, fluid would be expelled through the perforations and create a "showerhead" like effect to flush a user's eye.

The exemplary eye flushing system described herein may be used with other fluid sources than a traditional water bottle, without departing from the scope of the present invention. For example, the connecting portion 106 can be designed to mate with a canteen or a backpack-type personal hydration system. In general, it is contemplated that embodiments of the present invention are not limited to any particular portable water source but can be utilized with a variety of different sources.

Figure 3A:
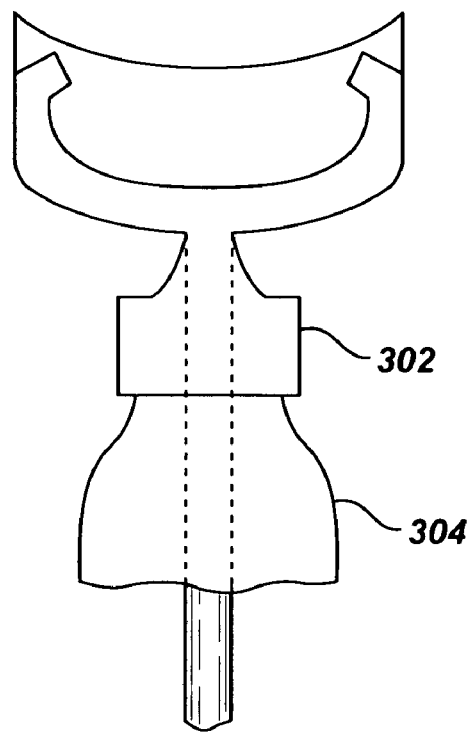
FIGS. 3A-3C show alternative embodiments of the present eye flushing system.
Figure 3B:
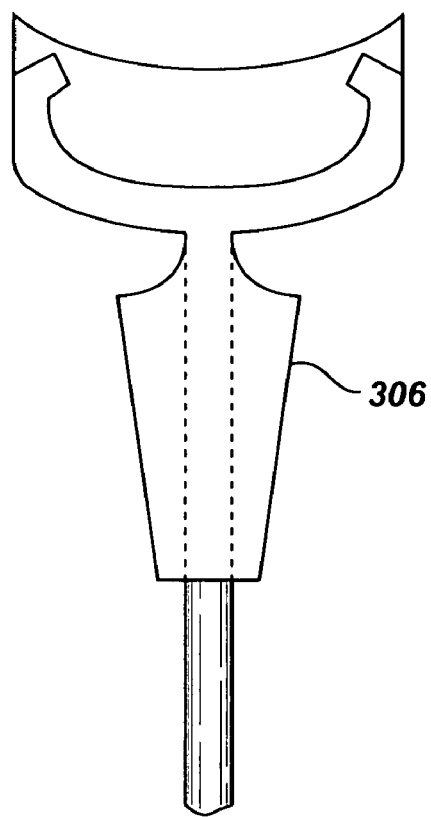

Accordingly, FIGS. 3A and 3B depict two different universal adapter systems to accommodate a variety of different fluid sources. In FIG. 3A, an elastomer skirt 304 is connected to a neck portion 302 of an eye cup. In operation, the elastomer stretches over the neck of a water bottle or similar water source to provide a fluid tight seal. Alternatively, FIG. 3B depicts a cork-type adapter that includes a tapered portion 306 that is forced into an opening of a water bottle or similar fluid source. The tapered portion 306 thus creates a friction seal that will not be overcome by the minimal pressures resulting from use of the eye flushing system.

Figure 3C:
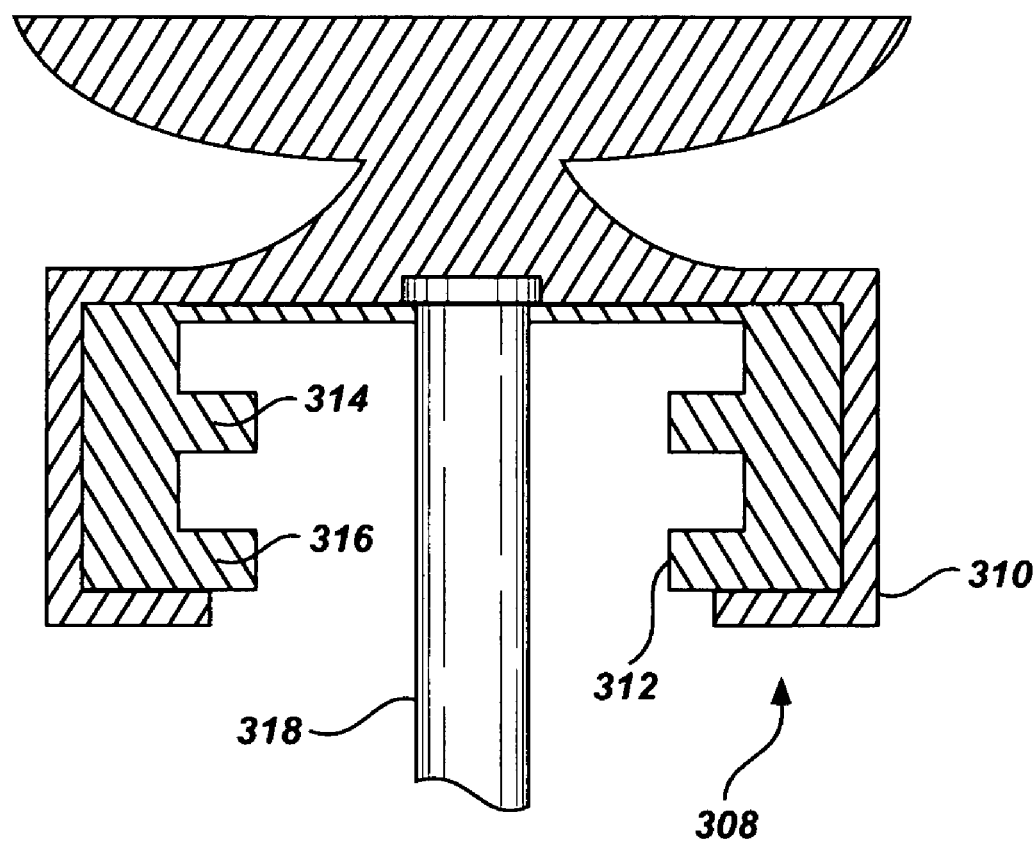

One additional configuration for the neck portion of the present adapter 103 is depicted in FIG. 3C. This neck portion 308 is particularly suited to standard water bottle sizes but does not require a threaded portion 108 as depicted in FIG. 1. In the arrangement of FIG. 3C, the neck portion has an outer housing 310 of relatively stiff and durable plastic or other material. Within the housing 310, a softer elastomeric material 312 is formed as a hollow cylinder and has some flexible properties and surrounds the area where the water delivery tube 318 is positioned. The material portion 312 does not have a smooth interior wall but instead has one or more protrusions 314, 316 that extend inwardly around the inside circumference of the material portion 312. The size of the material portion 312 is selected so that the protrusions 314, 316 are slightly compressed when pushed over the opening of a water bottle. Although the inside diameter created by the protrusions is slightly less than the outside diameter of a water bottle, because of their flexibility, the material portion 312 allows a water bottle opening to be pushed into the neck portion 308 while also acting like a gasket to form a fluid tight seal around the opening of the water bottle. While there are two protrusions 314, 316 depicted in FIG. 3C, more or less protrusions may be used without departing from the scope of the present invention. Additionally, a protrusion length of about ⅛ inch provides the flexibility to allow the water bottle to be inserted in the neck portion 308 and also provide a fluid-tight seal; however, it is apparent that other lengths may work as well depending on the specific material selected.

The system of FIG. 3C provides beneficial manufacturing possibilities. For example, the outside housing 310 which forms the neck portion and the eye-cup portion can be manufactured as two halves (along the major axis of the eye-cup portion). The material portion 312 can be manufactured as a unitary gasket having an opening through which the tube 318 can be inserted. To assemble, the gasket can be placed in one half of the housing and then the second half can be snapped on the first half, thereby securing the gasket. The two halves can be sealed together with adhesive, friction welding, other bonding techniques, or simply through some type of snap mechanism that can be easily molded.

The system described above has a variety of different uses. One exemplary use is for helping motorcycle riders. It is not uncommon for debris or grit to become lodged in the eyes of a motorcycle rider and it would be convenient to have an eye flushing system that is compactly stored, readily available, and can be used without a specialized water source. Thus, the rider can connect the system to a water bottle, lean over slightly at the waist and squeeze the water bottle to flush an eye. Because of the drain hole, the water will exit the eye cup away from the rider's body and not get on their clothes or bike. In this way, the rider's eye can be flushed without pouring water all over their face or clothes. Other potential users include, for example, landscape workers, soldiers in dusty and sandy environments, and backpackers.

If an alternative water source is used that does not allow the rider to squeeze the bottle, then the system can be used to deliver water to an eye via gravity simply by tilting the rider's head back and letting the water flow into the eye.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An adapter sized to fit an opening of a separate portable fluid container, the adapter comprising:
    a tube having a first end and a second end, wherein the tube is hollow along its length and has openings at the first end and the second end;
    an eye cup; and
    a neck portion configured to provide a fluid-tight seal with the opening of the separate portable fluid container,
    wherein the neck portion is connected to the eye cup and the first end of the tube such that the tube and the neck portion provide a fluid passageway from the separate portable fluid container to the eye cup; and
    wherein the second end of the tube is configured to extend into the separate portable fluid container; and
    wherein the eye cup further comprises:
        a portion in fluid communication with the opening at the first end of the tube;
        a first hollow arm having a first part extending outwardly from the portion of the eye cup, a second part extending upwardly, and a third part extending inwardly relative to the second part, wherein the second part is disposed between, and in fluid communication with, the first part and the third part; and
        a second hollow arm having a fourth part extending outwardly from the portion of the eye cup away from the first part of the first hollow arm, a fifth part extending upwardly, and a sixth part extending inwardly relative to the fifth part, wherein the fifth part is disposed between, and in fluid communication with the fourth part and the sixth part.

2. The adapter of claim 1, wherein the tube is flexible.

3. The adapter of claim 2, wherein the tube is flexible enough to coil within the separate portable fluid container when a length of the tube is larger than that of the separate portable fluid container.

4. The adapter of claim 1, wherein the tube includes an adjustable portion that changes a length of the tube.

5. The adapter of claim 1, wherein the eye cup further includes a drainage hole.

6. The adapter of claim 1, wherein the eye cup is generally elliptical in shape and has a major axis and a minor axis.

7. The adapter of claim 6,
    wherein the first part of the first hollow arm extends outwardly from the portion of the eye cup along the major axis of the eye cup; and
    wherein the fourth part of the second hollow arm extends outwardly from the portion of the eye cup along the major axis of the eye cup opposite the direction of the first part.

8. The adapter of claim 7, further comprising:
    a first delivery opening at an end of the third part opposite the second part and in fluid communication with the portion of the eye cup and the opening at the first end of the tube through the first, second, and third parts; and
    a second delivery opening at an end of the sixth part opposite the fifth part and in fluid communication with the portion of the eye cup and the opening at the first end of the tube through the fourth, fifth and sixth parts.

9. The adapter of claim 7, wherein the first and fourth parts are perforated such that the perforations are in fluid communication with the portion of the eye cup and the opening at the first end of the tube.

10. The adapter of claim 7, wherein the first, second, fourth and fifth parts are perforated such that the perforations are in fluid communication with the portion of the eye cup and the opening at the first end of the tube.

11. The adapter of claim 7, wherein the second part extends upwardly for a first height, wherein the fifth part extends upwardly for a second height, and wherein the first and second heights are equal.

12. The adapter of claim 7, wherein the third part extends inwardly at a first angle relative to the second part, wherein the sixth part extends inwardly at a second angle relative to the fifth part: and wherein the first and second angles are equal.

13. The adapter of claim 12, wherein the first and second angles are approximately 20 degrees.

14. The adapter of claim 1, wherein the third part and the sixth part are angled back towards the center of the eye cup.

15. The adapter of claim 1, wherein the neck portion further comprises:
    an outer housing;
    a hollow cylindrical portion, within the outer housing, having an inner surface and an outer surface;
    the inner surface of the hollow cylindrical portion including at least one compressible protrusion extending inwardly around the circumference of the inner surface such that the compressible protrusion is configured to form a tight seal around the opening of the separate portable fluid container by compression of the at least one compressible protrusion when the neck portion is pushed onto the opening of the separate portable fluid container.

16. The adapter of claim 15, wherein the inner surface of the hollow cylindrical portion includes at least two compressible protrusions.

17. The adapter of claim 15, wherein the inside diameter of the compressible protrusion is less than the outside diameter of the opening of the separate portable fluid container.

18. The adapter of claim 15, wherein the neck portion is configured to form a tight seal around a non-threaded opening of the separate portable fluid container.

19. The adapter of claim 15, wherein the outer housing of the neck portion comprises two halves that are configured to be sealed or snapped together around the hollow cylindrical portion of the neck portion.

* * * * *